US010285404B2

(12) United States Patent
Hemminghaus et al.

(10) Patent No.: US 10,285,404 B2
(45) Date of Patent: May 14, 2019

(54) GLYPHOSATE COMPOSITION FOR DICAMBA TANK MIXTURES WITH IMPROVED VOLATILITY

(71) Applicant: Monsanto Technology LLC, St. Louis, MO (US)

(72) Inventors: John Hemminghaus, St. Louis, MO (US); Alison MacInnes, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 779 days.

(21) Appl. No.: 14/191,932

(22) Filed: Feb. 27, 2014

(65) Prior Publication Data

US 2014/0249026 A1    Sep. 4, 2014

Related U.S. Application Data

(60) Provisional application No. 61/769,943, filed on Feb. 27, 2013.

(51) Int. Cl.
*A01N 25/30* (2006.01)
*A01N 37/40* (2006.01)
*A01N 57/20* (2006.01)

(52) U.S. Cl.
CPC ............ *A01N 57/20* (2013.01); *A01N 37/40* (2013.01)

(58) Field of Classification Search
CPC ......... A01N 57/20; A01N 25/30; A01N 37/40
USPC ....................................................... 504/127
See application file for complete search history.

(56) References Cited

U.S. PATENT DOCUMENTS

| | | |
|---|---|---|
| 2,505,059 A | 4/1950 | Moore |
| 3,013,054 A | 12/1961 | Richter |
| 3,276,856 A | 10/1966 | Esposito |
| 3,594,151 A | 7/1971 | Sprayberry et al. |
| 3,600,407 A | 8/1971 | Levin et al. |
| 3,713,404 A | 1/1973 | Lavo et al. |
| 3,751,239 A | 8/1973 | McNulty et al. |
| 3,799,758 A | 3/1974 | Franz |
| 3,852,340 A | 12/1974 | Reck et al. |
| 3,870,732 A | 3/1975 | Hokama |
| 3,910,974 A | 10/1975 | Hokama |
| 3,923,849 A | 12/1975 | Hokama |
| 4,022,610 A | 5/1977 | Hokama |
| 4,405,531 A | 9/1983 | Franz |
| 4,445,927 A | 5/1984 | Gimesi et al. |
| 4,534,783 A | 8/1985 | Beestman |
| 4,546,196 A | 10/1985 | Luteri et al. |
| H303 H | 7/1987 | Malik et al. |
| 4,692,184 A | 9/1987 | Lee |
| 4,729,781 A | 3/1988 | Williams |
| 4,936,900 A | 6/1990 | Hyson |
| 4,936,901 A | 6/1990 | Surgant, Sr. et al. |
| 5,004,863 A | 4/1991 | Umbeck |
| 5,015,580 A | 5/1991 | Christou et al. |
| 5,035,738 A | 7/1991 | Burns et al. |
| 5,152,823 A | 10/1992 | Albercht et al. |
| 5,159,135 A | 10/1992 | Umbeck |
| 5,175,353 A | 12/1992 | Jones et al. |
| 5,221,319 A | 6/1993 | Van Haften et al. |
| 5,229,354 A | 7/1993 | Narayanan et al. |
| 5,229,355 A | 7/1993 | Chaudhuri et al. |
| 5,231,070 A | 7/1993 | Narayanan et al. |
| 5,250,500 A | 10/1993 | Jones et al. |
| 5,266,553 A | 11/1993 | Champion et al. |
| 5,283,228 A | 2/1994 | Narayanan et al. |
| 5,317,003 A | 5/1994 | Kassebaum et al. |
| 5,384,253 A | 1/1995 | Krzyzek et al. |
| 5,416,011 A | 5/1995 | Hinchee et al. |
| 5,434,783 A | 7/1995 | Pal et al. |
| 5,436,223 A | 7/1995 | Mulqueen et al. |
| 5,463,174 A | 10/1995 | Moloney et al. |
| 5,508,184 A | 4/1996 | Negrutiu et al. |
| 5,518,908 A | 5/1996 | Corbin et al. |
| 5,538,880 A | 6/1996 | Lundquist et al. |
| 5,550,318 A | 8/1996 | Adams et al. |
| 5,565,409 A | 10/1996 | Sato et al. |
| 5,569,834 A | 10/1996 | Hinchee et al. |
| 5,591,616 A | 1/1997 | Hiei et al. |
| 5,631,152 A | 5/1997 | Fry et al. |
| 5,668,085 A | 9/1997 | Forbes et al. |
| 5,670,454 A | 9/1997 | Grossmann et al. |
| 5,703,015 A | 12/1997 | Berger et al. |
| 5,733,848 A | 3/1998 | Luteri |
| 5,750,468 A | 5/1998 | Wright et al. |
| 5,824,877 A | 10/1998 | Hinchee et al. |
| 5,834,006 A | 11/1998 | Smith et al. |
| 5,877,112 A | 3/1999 | Roberts |
| 5,883,046 A | 3/1999 | Luteri |

(Continued)

FOREIGN PATENT DOCUMENTS

| | | |
|---|---|---|
| AU | 10073/92 B | 10/1992 |
| AU | 2010202620 A1 | 7/2010 |

(Continued)

OTHER PUBLICATIONS

Material Safety Data Sheet regarding Amine 4 2,4-D Weed Killer prepared by Registrations and Regulatory Affairs, Date of Issue Dec. 14, 2012, 3 pages.

(Continued)

*Primary Examiner* — Mina Haghighatian
*Assistant Examiner* — Mei Ping Chui
(74) *Attorney, Agent, or Firm* — Stinson Leonard Street LLP; Erin C. Robert

(57) ABSTRACT

Herbicidal concentrate compositions containing glyphosate salts and tank mix compositions containing a combination of glyphosate salt and dicamba salt herbicides are described. A method of preparing a tank mix composition comprising a glyphosate component and a dicamba component is also described. The method includes combining a glyphosate concentrate composition, a dicamba composition comprising one or more salts of dicamba and dilution water to form the tank mix composition. The glyphosate concentrate composition comprises a glyphosate salt selected from the group consisting of the monoethanolamine salt, the potassium salt, and mixtures thereof at a glyphosate loading of at least about 240 grams acid equivalent per liter (g a.e./l), and the pH of a 5 wt. % acid equivalent dilution of the glyphosate concentrate composition is from about 5 to about 6.5.

30 Claims, No Drawings

(56) References Cited

U.S. PATENT DOCUMENTS

| | | |
|---|---|---|
| 5,883,048 A | 3/1999 | Morre et al. |
| 5,965,487 A | 10/1999 | Flahive |
| 5,981,840 A | 11/1999 | Zhao et al. |
| 5,998,332 A | 12/1999 | Sato et al. |
| 6,030,923 A | 2/2000 | Okano et al. |
| 6,060,432 A | 5/2000 | Adams et al. |
| 6,063,733 A | 5/2000 | Berger et al. |
| 6,107,246 A | 8/2000 | Wiley |
| 6,121,199 A | 9/2000 | Berger et al. |
| 6,133,199 A | 10/2000 | Soula et al. |
| 6,160,208 A | 12/2000 | Lundquist et al. |
| 6,177,414 B1 | 1/2001 | Tomalia et al. |
| 6,228,807 B1 | 5/2001 | Kuchikata et al. |
| 6,245,713 B1 | 6/2001 | Brinker et al. |
| 6,277,788 B1 | 8/2001 | Wright |
| 6,300,323 B1 | 10/2001 | Haga et al. |
| 6,337,078 B1 | 1/2002 | Levy |
| 6,384,301 B1 | 5/2002 | Martinelli et al. |
| 6,399,861 B1 | 6/2002 | Anderson et al. |
| 6,403,865 B1 | 6/2002 | Koziel et al. |
| 6,410,783 B1 | 6/2002 | Peterson et al. |
| 6,417,140 B1 | 7/2002 | Patel |
| 6,436,874 B1 | 8/2002 | Kuah et al. |
| 6,455,473 B2 | 9/2002 | Wright |
| RE37,866 E | 10/2002 | Wright et al. |
| 6,500,783 B1 | 12/2002 | Bryson et al. |
| 6,569,809 B1 | 5/2003 | Sato et al. |
| 6,579,831 B1 | 6/2003 | Harwell |
| 6,586,367 B2 | 7/2003 | Lee et al. |
| 6,677,276 B1 | 1/2004 | Hacker et al. |
| 6,713,433 B2 | 3/2004 | Jimoh |
| 6,723,681 B2 | 4/2004 | Hacker et al. |
| 6,774,087 B1 | 8/2004 | Nakayama et al. |
| 6,906,004 B2 | 6/2005 | Parrish et al. |
| 6,939,555 B2 | 9/2005 | Volgas et al. |
| 7,135,437 B2 | 11/2006 | Pallas et al. |
| 7,223,718 B2 | 5/2007 | Smiley |
| 7,431,845 B2 | 10/2008 | Manek et al. |
| 7,695,541 B1 | 4/2010 | Frizzell et al. |
| 2002/0107149 A1 | 8/2002 | Volgas et al. |
| 2002/0123430 A1 | 9/2002 | Xu et al. |
| 2002/0155953 A1 | 10/2002 | Brigance |
| 2003/0004063 A1 | 1/2003 | Jimoh |
| 2003/0022791 A1 | 1/2003 | Asrar et al. |
| 2003/0087764 A1 | 5/2003 | Pallas |
| 2003/0104943 A1 | 6/2003 | Lennon et al. |
| 2004/0077499 A1 | 4/2004 | Graham et al. |
| 2004/0138176 A1 | 7/2004 | Miles |
| 2005/0026780 A1 | 2/2005 | Parrish |
| 2006/0019828 A1 | 1/2006 | Becher et al. |
| 2006/0040828 A1 | 2/2006 | Mao et al. |
| 2006/0270556 A1 | 11/2006 | Wright et al. |
| 2007/0093462 A1 | 4/2007 | Rogers et al. |
| 2007/0149409 A1 | 6/2007 | Burnet et al. |
| 2007/0184980 A1 | 8/2007 | Roberts et al. |
| 2007/0259789 A1 | 11/2007 | Huchet et al. |
| 2008/0119361 A1 | 5/2008 | Feng et al. |
| 2008/0153706 A1 | 6/2008 | Frisch et al. |
| 2008/0182773 A1 | 7/2008 | Gauweiler et al. |
| 2008/0207452 A1 | 8/2008 | Kramer et al. |
| 2008/0207453 A1 | 8/2008 | Kramer et al. |
| 2009/0041813 A1 | 2/2009 | Bouillo et al. |
| 2009/0062127 A1 | 3/2009 | Liu |
| 2009/0093366 A1 | 4/2009 | Wright et al. |
| 2009/0170702 A1 | 7/2009 | Yoshii et al. |
| 2010/0113274 A1 | 5/2010 | Hemminghaus et al. |
| 2010/0273654 A1 | 10/2010 | Li et al. |
| 2010/0331182 A1 | 12/2010 | Zhang et al. |
| 2011/0019652 A1 | 1/2011 | Atwal |
| 2011/0034332 A1 | 2/2011 | Becher et al. |
| 2011/0263430 A1 | 10/2011 | Seifert-Higgins et al. |
| 2011/0275517 A1 | 11/2011 | Satchivi et al. |
| 2012/0142532 A1 | 6/2012 | Wright et al. |
| 2012/0184434 A1 | 7/2012 | Xu et al. |
| 2014/0171321 A1 | 6/2014 | Wright et al. |
| 2014/0309114 A1 | 10/2014 | Zheng et al. |
| 2015/0164082 A1 | 6/2015 | MacInnes et al. |
| 2016/0366878 A1 | 12/2016 | Wright et al. |

FOREIGN PATENT DOCUMENTS

| | | |
|---|---|---|
| CA | 1293974 C | 1/1992 |
| CA | 2340240 A1 | 2/2000 |
| CA | 2729738 A1 * | 1/2010 |
| CN | 1513326 A | 7/2004 |
| DE | 4030687 A1 | 5/1991 |
| DE | 19836737 A1 | 5/1991 |
| DE | 19836660 | 2/2000 |
| DE | 19836684 | 2/2000 |
| DE | 19836700 | 2/2000 |
| EP | 0375624 A1 | 6/1990 |
| EP | 290416 A2 | 6/1993 |
| EP | 360441 A1 | 4/1994 |
| EP | 0808569 A1 | 11/1997 |
| EP | 1023832 A1 | 8/2000 |
| GB | 1262123 A | 2/1972 |
| GB | 2267825 A | 12/1993 |
| RU | 2208930 C1 | 7/2003 |
| RU | 2366176 C2 | 9/2009 |
| RU | 2384064 C1 | 3/2010 |
| RU | 2395203 C1 | 7/2010 |
| RU | 2408188 C1 | 1/2011 |
| WO | 92/12637 A1 | 9/1992 |
| WO | 9212637 A1 | 9/1992 |
| WO | 95/16351 A1 | 6/1995 |
| WO | 97/31535 A2 | 9/1997 |
| WO | 99/00013 A2 | 1/1999 |
| WO | 9905914 A1 | 2/1999 |
| WO | 00/08936 A1 | 2/2000 |
| WO | 0005951 A1 | 2/2000 |
| WO | 0005952 A1 | 2/2000 |
| WO | 00/15037 A1 | 3/2000 |
| WO | 00/30451 A1 | 6/2000 |
| WO | 2000030452 A1 | 6/2000 |
| WO | 00/64257 A1 | 11/2000 |
| WO | 00/67571 A1 | 11/2000 |
| WO | 01/17358 A1 | 3/2001 |
| WO | 01/35740 A2 | 5/2001 |
| WO | WO 01/89302 A2 * | 11/2001 |
| WO | 02/21924 A2 | 3/2002 |
| WO | 02/096199 A2 | 12/2002 |
| WO | 2002102153 A2 | 12/2002 |
| WO | 03/013241 A1 | 2/2003 |
| WO | 03/024218 A1 | 3/2003 |
| WO | 2004/093546 A1 | 11/2004 |
| WO | 2005/087007 A1 | 9/2005 |
| WO | 2005115144 A1 | 12/2005 |
| WO | 2007110355 A2 | 10/2006 |
| WO | 2008030749 A2 | 3/2008 |
| WO | 2008101818 A2 | 8/2008 |
| WO | 2008/106118 A2 | 9/2008 |
| WO | 2009060026 A2 | 5/2009 |
| WO | 2010046422 A2 | 4/2010 |
| WO | 2010071936 A1 | 7/2010 |
| WO | 2010102102 A1 | 9/2010 |
| WO | 2010/147966 A1 | 12/2010 |
| WO | 2011019652 A2 | 2/2011 |
| WO | WO 2011/019652 A2 * | 2/2011 |
| WO | 2011/026800 A2 | 3/2011 |
| WO | 2011039172 A2 | 4/2011 |
| WO | 2012040785 A1 | 4/2012 |
| WO | 2012104237 A2 | 8/2012 |
| WO | 2012163824 A1 | 12/2012 |
| WO | 2013/063357 A3 | 2/2013 |
| WO | 2013184622 A2 | 12/2013 |
| WO | PCT/US2014/018829 * | 2/2014 |
| WO | WO 2014/134235 A1 * | 9/2014 |

OTHER PUBLICATIONS

Safety Data Sheet—Clarity (Version 3.0), BASF The Chemical Company, May 2, 2013, 9 pages.

(56) References Cited

OTHER PUBLICATIONS

Hartzler, Dicamba Volatility, Iowa State University Weed Science Online (http://www.weeds.iastate.edu/mgmt/2001/dicambavolatility.htm), 2001, 4 pages.
Purdue, Herbicide Formulations (http://web.archive.org/web/*/http://www.agriculture.purdue.edu/fnr/html/faculty/holt/NRCASupplement.pdf) from 2007, 19 pages.
Serafini, dicamba, diglycolamine salt (Clarity) Active Ingredient Registration 6/00, (http://pmep.cce.cornell.edu/profiles/herb-growthreg/dalapon-ethephon/diglycolamine/Diglycolamine_600.html), downloaded Apr. 6, 2014, 3 pages.
Agrian, Buffer Protect, Westbridge Agricultural Products, http://www.agrian.com/labelcenter, downloaded Jan. 17, 2013, 2 pages.
Behrens, R., et al., "Dicamba Volatility," 1979, Weed Science, 27/5:486-493.
Branham, B.E., et al., "Drift and Volatility of Broadleaf Herbicides," pp. 126-129.
CLARITY®, Safety Data Sheet, BASF, Revised Aug. 14, 2006, 7 pages.
CLIMB® Alkalinity Agent, Wilbur-Ellis Company, CA Reg. No. 2935-50181, WA Reg. No. 2935-09001, F-091809-1, 2 pages.
Dion, H.M., et al., "Competitive Sorption Between Glyphoste and Inorganic Phosphate on Clay Minerals and Low Organic Matter Soils," 2001, J Radioanaly and Nucl Chem, 249/2:385-390.
Foy, C.L., et al., "Effect of Inhibitors and herbicides on Tricarboxylic Acid Cycle Substrate Oxidation by Isolated Cucumber Mitochondria," 1965, Weeds, 13/3:226-231.
Hall, J.K., et al., "Dicamba Mobility in Conventionally Tilled and Non-Tilled Soils," 1994, Soil & Tillage Res, 30:3-17.
Hartzler, B., "Dicamba Volatility," 2001, Weed Science Online, Iowa State University, Downloaded Mar. 27, 2014, 4 pages.
Hoefer, R.H., et al., "Absorption of Dicamba in Soybeans as Effected by Formulation and Suractants," 1979, North Central Weed Control Conference, Abstract, pp. 4-5.
LUPASOL®, Polyethylenimines for Creative Connections, BASF, EVD 0116e Nov. 2005, pp. 6.
LUPASOL® Products, Technical Information, Feb. 2008, BASF, 12 pages.
Material Safety Data Sheet, BANVEL®, EPA Reg. No. 51036-289, BASF, Prepared Jul. 14, 1999, 3 pages.
Material Safety Data Sheet, BANVEL II®, BASF, Revised Nov. 30, 2006, 5 pages.
Material Safety Data Sheet, Blend of Di-potassium Phosphate, Nitrogen, and Ag-Phite (DKP xtra), Product No. 3-18-20, Plant Food Systems, Inc., Undated, 1 page.
Material Safety Data Sheet, DICAMBA 480 Manufacturing Concentrate, Reg. No. 24774, Syngenta Crop Protection Canada, Inc., MSDS Preparation Date Dec. 31, 2008, 6 pages.
Nalewaja, J.D., et al., "2,4-D Amine Antagonism by Salts," 1991, Weed Technology, 5/4:873-880.
Nalewaja, J.D., et al., "Salt Antagonism of Glyphosate," 1991, Weed Science, 39:622-628.
Owen, M.D.K., et al., "Evaluation of Nicosulfuron, Rimsulfuron, and Pyridate Applied Postemergence for Weed Control in Corn," 1995, NCWSS Research Report-V.52, Ames, IA, 149-152.
Peniuk, M.G., et al., "Absorption, Translocation, and Metabolosm are not the Basis for Differential Selectivity of Wild Mustart (*Sinapis argensis* L.)," 1992, WSSA Abstracts, No. 165, 32:55.
Petersen, P.J., et al., "Dicamba Absorption and Translocation as Influenced by Formulation and Surfactant," 1985, Weed Science, 33:717-720.
Poovaiah, B.W., et al., "Effects of Inorganic Salts on Tissue Permeability," 1976, Plant Physiol., 58:182-185.
Quimby, P.C., Jr., et al., "Selectivity of Dicamba in Wheat and Wild Buckwheat," 1971, Weed Science, 1915:598-601.
Ramirez-Ortega, R., et al., "Enhancement Effect of N, P and K on Glyphosate for Broomrape (*Orobanche crenata* Forsk.) Control in Faba Bean (*Vicia faba* L.)," 1992, FABIS Newsletter 31, pp. 37-39.
Sargent, J.A., "Chapter 10 Relatiohnship of Selectivity to Uptake and Movement," 1976, Herbicides, 2nd Ed, vol. 2, 303-312, 12 pages.
Scott, P.C., "Separation of Effects of Auxin and Ethylene in Pea Roots," 1970, Nature, 226:1366-1367.
Sprankle, P., et al., Rapid Inactivation of Glyphosate in the Soil, 1975, Weed Science, 2313:224-228.
Wauchope, R.D., et al, "The SCS/ARS/CES Pesticide Properties Database for Environmental Decision-Making," 1992, Rvws of Environ Contam and Toxic, 123:1-164.
International Preliminary Report on Patentability issued in International PCT Application No. PCT/US2010/044873, dated Aug. 10, 2009, 16 pages.
International Search Report and Written Opinion issued in International PCT Application No. PCT/US2010/044873, dated May 10, 2011, 22 pages.
International Search Report and Written Opinion issued in International PCT Application No. PCT/US2013/043995, dated Oct. 24, 2013, 9 pages.
International Search Report and Written Opinion issued in International PCT Application No. PCT/US2014/018829, dated Jun. 2, 2014, 10 pages.

\* cited by examiner

GLYPHOSATE COMPOSITION FOR DICAMBA TANK MIXTURES WITH IMPROVED VOLATILITY

REFERENCE TO RELATED APPLICATIONS

This application claims the benefit of U.S. Provisional Application Ser. No. 61/769,943, filed Feb. 27, 2013, the entire contents of which are incorporated herein by reference.

FIELD OF THE INVENTION

The present invention generally relates to tank mix compositions containing a combination of glyphosate salt and dicamba salt herbicides and methods for preparing the tank mix. The present invention also relates to herbicidal concentrate compositions containing glyphosate salts.

BACKGROUND OF THE INVENTION

Glyphosate is well known in the art as an effective post-emergent foliar-applied herbicide. In its acid form (N-(phosphonomethyl)glycine), glyphosate has the following structure:

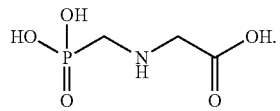

Glyphosate acid is relatively insoluble in water (about 1.16 wt. % at 25° C.). For this reason it is typically formulated as a water-soluble salt. For example, herbicidal concentrate compositions and application formulations containing, for example, the sodium, potassium, ammonium, isopropylamine, or monoethanolamine salts of glyphosate are well known in the art.

Herbicidal compositions and formulations comprising glyphosate or glyphosate salt are useful for suppressing the growth of, or killing, unwanted plants such as grasses, weeds and the like. Glyphosate is typically applied to the foliage of the target plant. After application, glyphosate is absorbed by the foliar tissue of the plant and translocated throughout the plant. Glyphosate noncompetitively blocks an important biochemical pathway which is common to virtually all plants, but which is absent in animals. Although glyphosate is very effective in killing or controlling the growth of unwanted plants, the uptake (i.e., absorption) of glyphosate by plant foliar tissue and translocation of glyphosate throughout the plant is relatively slow. Visual symptoms that a plant has been treated with glyphosate may not appear until one week or more after treatment.

Dicamba has proven to be a particularly effective auxin herbicide. In its acid form, dicamba has the following structure:

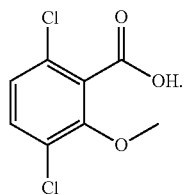

Like glyphosate, dicamba is typically formulated as a salt, such as the sodium, potassium, diethanolamine, isopropylamine, diglycolamine, or dimethylamine salt.

Generally, auxin herbicides such as dicamba mimic or act like natural auxin plant growth regulators. Auxin herbicides appear to affect cell wall plasticity and nucleic acid metabolism, which can lead to uncontrolled cell division and growth. The injury symptoms caused by auxin herbicides include epinastic bending and twisting of stems and petioles, leaf cupping and curling, and abnormal leaf shape and venation.

Off-site movement is sometimes associated with dicamba and other auxin herbicides. Under certain conditions of application, dicamba can migrate from the application site to adjacent crop plants, such as soybeans and cotton, where contact damage to sensitive plants can occur. Various strategies have been suggested to reduce off-site movement of dicamba including formulating dicamba in the form of certain mineral or amine salts, encapsulating dicamba with a polymeric coating, and complexing with a polybasic polymer.

Tank mixes of dicamba and glyphosate are known in the art. For example, an herbicidal concentrate containing 480 grams acid equivalent per liter (g a.e./l) of the dimethylamine salt of dicamba, sold under the trade name BANVEL, is available from BASF. As used herein, the term "acid equivalent" or "a.e." refers to the amount of herbicide present without taking into account the weight of the counter-ion of the salt species present. The package instructions for use of this concentrate of dicamba indicate that dicamba can be tank mixed with other diluted herbicides including glyphosate. Tank mixing of dicamba and glyphosate according to these instructions provides a spray solution having a total herbicide concentration up to about 100 g a.e./l. Patent literature also mentions herbicidal compositions containing glyphosate and dicamba. For example, see U.S. Patent Application Publication No. US 2006/0019828 A1 and U.S. Pat. Nos. 6,277,788 and 6,455,473.

Addition of glyphosate to some tank mixes of dicamba has been known to negatively affect dicamba volatility and increase off-site movement of dicamba. Accordingly, there remains a need for glyphosate compositions that can be tank mixed with dicamba that will reduce the effects on dicamba volatility resulting from the incorporation of glyphosate. Similarly, there remains a need for a tank mix and method of preparing the tank mix, which has an acceptable dicamba volatility profile.

Further, with the development of transgenic plants including stacked glyphosate-tolerant and dicamba-tolerant traits, tank mix compositions containing a combination of glyphosate and dicamba are particularly beneficial and convenient for control of unwanted plants. Thus, there is a need for concentrate compositions containing glyphosate that can be economically produced while having sufficient stability and that are formulated to provide effective spray formulation solutions for application to unwanted plants. There also remains a need for methods of preparing glyphosate/dicamba tank mixes that reduce or eliminate the increase in dicamba volatility as a result of adding glyphosate.

As will be clear from the disclosure that follows, these and other benefits are provided by the present invention.

SUMMARY OF THE INVENTION

Generally, the present invention relates to aqueous herbicidal concentrate compositions comprising glyphosate salt herbicide and methods of preparing herbicidal tank mixes using the concentrate compositions. In various aspects, the present invention includes a method of preparing an aqueous tank mix composition comprising a glyphosate salt and a dicamba salt. The method comprises combining an aqueous glyphosate concentrate composition, a dicamba composition comprising one or more salts of dicamba and dilution water to form the tank mix composition. The glyphosate concentrate composition comprises a glyphosate salt selected from the group consisting of the monoethanolamine salt, the potassium salt, and mixtures thereof at a glyphosate loading of at least about 240 g a.e./l. The pH of a 5 wt. % acid equivalent dilution of the glyphosate concentrate composition is from about 5 to about 6.5.

In another aspect, the present invention relates to tank mix composition comprising a mixture of monobasic and dibasic salts of glyphosate; one or more salts of dicamba; dilution water; and a surfactant. The tank mix composition has a total herbicide concentration no greater than about 10% by weight a.e. and a pH from about 5 to about 6.5.

Other objects and features will be in part apparent and in part pointed out hereinafter.

DESCRIPTION OF THE PREFERRED EMBODIMENTS

In general, the present invention is directed to aqueous herbicidal concentrate compositions comprising glyphosate salt herbicide, tank mix compositions prepared in part with the glyphosate concentrate compositions, and methods of preparing the tank mixes. The glyphosate concentrate composition can be tank mixed with dicamba to provide an effective spray formulation solution that conveniently reduces the effects on dicamba volatility compared to conventional glyphosate/dicamba tank mixes. A glyphosate concentrate composition that is capable of reducing dicamba volatility tank mixing effects and associated off-site movement of dicamba can beneficially provide a glyphosate/dicamba tank mix that is more effective for controlling unwanted plants while reducing injury to sensitive crops or non-target plants. Also, a glyphosate concentrate composition that is capable of controlling dicamba volatility tank mixing effects eliminates or reduces the need for employing other means for controlling dicamba volatility. Further, the storage space and associated packaging that would otherwise be required for more dilute compositions is reduced. The smaller volume reduces space required to store and transport the concentrate composition prior to sale or use.

A further aspect of the present invention is to provide stable and compatible tank mix compositions containing a combination of glyphosate salt and dicamba salt herbicides that are relatively clear and do not appreciably separate into phases or form precipitates upon standing or storage. A stable and compatible tank mix composition beneficially provides a uniform spray formulation solution without the need for excessive agitation.

Another aspect of the present invention is to provide a tank mix composition containing glyphosate salt, dicamba salt, and at least one surfactant. Incorporation of at least one surfactant beneficially increases the effectiveness of the glyphosate and dicamba active ingredients upon application to the foliar tissues of unwanted plants. In accordance with various aspects of the present invention, the aqueous glyphosate concentrate composition comprises a glyphosate component comprising one or more water-soluble salts of glyphosate. The glyphosate concentrate composition may be used in accordance with methods of the present invention for preparing tank mix compositions. The method comprises combining the aqueous glyphosate concentrate composition, a dicamba composition comprising one or more salts of dicamba and dilution water to form the tank mix.

Generally, the pH of the glyphosate concentrate composition is greater than about 5. The pH of the aqueous glyphosate concentrate composition is an important aspect of the present invention. The pH of a glyphosate concentrate composition is one factor that affects the compatibility between glyphosate and co-herbicides in tank mix compositions, the total herbicide loading that can be achieved in the concentrate, and the ability to incorporate a wide range surfactants into a stable glyphosate concentrate composition. Typically, conventional glyphosate concentrates are formulated as monobasic glyphosate salt solutions having a pH around 4 to 5. When these concentrates are used in tank mixes, the tribasic functionality of glyphosate is capable of buffering the pH of the tank mix solution near or within this pH range. For example, when dicamba formulations, which usually have a pH from about 7 to 8, are tank mixed with conventional glyphosate concentrate compositions, the pH of the tank mix is buffered by the glyphosate to around 4 to 5.

It has been observed that the volatility of some dicamba formulations increases when tank mixed with glyphosate. As explained above, the pH of the glyphosate/dicamba tank mix is typically acidic and less than conventional standalone dicamba solution, which is at neutral or slightly basic pH. Accordingly, without being bound by theory, the pH of a solution containing dicamba is believed to be a factor that affects the volatility profile of dicamba and the potential for offsite movement of dicamba.

Applicants have discovered that when certain aqueous glyphosate concentrate compositions are neutralized to a greater degree (e.g., neutralized using a molar excess of base to fully neutralize the acidic site of glyphosate having the lowest pKa, but less than two molar equivalents of base to glyphosate), the concentrates are capable of reducing the increase in dicamba volatility typically realized upon tank mixing the herbicides. Applicants have discovered that certain glyphosate concentrate compositions that are neutralized to a degree where the dilute pH is from about 5.0 to about 6.5, from about 5.2 to about 6.5, from about 5.5 to about 6.5, from about 5 to about 6, 5.2 to about 6, from about 5.5 to about 6, from about 5.2 to 5.8, or from about 5.2 to about 5.6 are capable of reducing dicamba volatility when tank mixed with dicamba. The dilute pH of the herbicidal concentrate compositions refers to pH of the concentrate when diluted to a concentration of 5 wt. % glyphosate acid equivalent using conventional pH measuring equipment (e.g., by immersing the probe of a pH meter into the dilute solution). Since glyphosate is neutralized to a greater degree, the concentrate composition contains a mixture of monobasic and dibasic salts of glyphosate. Thus, in various embodiments, the molar ratio of monobasic glyphosate salt to dibasic glyphosate salt is from about 1:1 to about 10:1, from about 1:1 to about 5:1, from about 1:1 to about 4:1, from about 1:1 to about 3:1, from about 1:1 to about 2:1, or from about 1.5:1 to about 3:1.

The mixture of monobasic and dibasic glyphosate salts may be referred to by the approximate number of acidic sites that are neutralized. For example, when the ratio of monobasic glyphosate salt to dibasic glyphosate salt is about 1:1, the mixture of the glyphosate salts may be referred to as the sesqui-salt of glyphosate (i.e., 1.5 salt). Or, when the ratio of monobasic glyphosate salt to dibasic glyphosate salt is, for instance, about 2:1 or about 3:1, then the mixture of salts may be referred to as the 1.33 and 1.25 salts of glyphosate, respectively. Accordingly, in various embodiments, the glyphosate concentrate composition contains a salt of glyphosate of from about the 1.1 salt to about the sesqui-salt, from about the 1.1 salt to about the 1.4 salt, from about the 1.2 salt to about the sesqui-salt, from about the 1.2 salt to about the 1.4 salt, from about the 1.25 salt to about the sesqui-salt, or from about the 1.25 salt to about the 1.4 salt. In some embodiments, the glyphosate concentrate composition contains the (approximately) 1.2, 1.25, 1.33, 1.4, or sesqui-salt of glyphosate.

Any base or mixture of bases that is capable of neutralizing one or more acidic sites of glyphosate may be used as the neutralizing base. For example, neutralizing bases include ammonia, hydroxides such alkaline or alkaline earth hydroxides, amine compounds such monoethanolamine and isopropylamine, mixtures of these bases, and so on. In various embodiments, the neutralizing base is a monoacidic base such as potassium hydroxide or monoethanolamine. In some embodiments, a mixture of bases may be used as the neutralizing base to prepare a mixed salt of glyphosate.

While the pH of the glyphosate concentrate composition is one factor that may affect dicamba volatility in tank mixes, it has been discovered that certain salts of glyphosate, when used at higher pH, are more effective in reducing dicamba volatility. Glyphosate salts generally include mono, di- or tribasic and include ammonium (e.g., mono-, di- or triammonium), alkali metal (e.g., potassium or sodium), sulfonium (e.g., mono-, di- or trimethylsulfonium) and organic ammonium salts of N-(phosphonomethyl)glycine (i.e., glyphosate acid). The organic ammonium salts, commonly referred to as amine salts, can comprise aliphatic or aromatic amine salts and can include primary, secondary, tertiary or quaternary amine salts. Representative examples of such organic amine salts include isopropylamine, n-propylamine, ethylamine, dimethylamine, monoethanolamine, ethylenediamine and hexamethylenediamine salts of N-(phosphonomethyl)glycine. In particular, certain alkali metal and monoethanolamine salts of glyphosate have been found to be especially suitable for achieving high herbicidal loadings in the glyphosate concentrate compositions of the present invention and when used at higher pH are more effective in reducing dicamba volatility in tank mixes containing glyphosate and dicamba.

Accordingly, in various embodiments, the aqueous glyphosate concentrate composition of the present invention comprises a glyphosate component comprising a glyphosate salt selected from the group consisting of an alkali salt (e.g., the potassium and/or sodium salt), monoethanolamine salt and mixtures thereof. In some embodiments, the glyphosate herbicidal concentrate contains glyphosate in the form of the potassium salt, monoethanolamine salt, or mixtures thereof. In certain embodiments, the glyphosate herbicidal concentrate contains glyphosate in the form of the potassium salt. In other embodiments, the glyphosate herbicidal concentrate contains glyphosate in the form of the monoethanolamine salt.

In some embodiments, the glyphosate herbicidal concentrate composition contains a salt of glyphosate wherein the salt-forming cation does not contain ammonium and/or does not contain a nitrogen atom. In these and other embodiments, the glyphosate herbicidal concentrate composition does not contain the sodium salt of glyphosate.

In accordance with the present invention, the aqueous glyphosate concentrate compositions provide a high total active herbicide loading of glyphosate salt. Typically, the total glyphosate loading of the concentrate is at least about 240 g/l, at least about 300 g/l, at least about 360 g/l, at least about 380 g/l, at least about 400 g/l, at least about 410 g/l, at least about 420 g/l, at least about 430 g/l, at least about 440 g/l, at least about 450 g/l, at least about 460 g/l, at least about 470 g/l, at least about 480 g/l, at least about 490 g/l, at least about 500 g/l, at least about 510 g/l, at least about 520 g/l, or at least about 530 g/l on an acid equivalent basis. In various embodiments, the total glyphosate loading of the concentrate is from about 360 g/l to about 550 g/l, from about 380 g/l to about 540 g/l, from about 400 g/l to about 540 g/l, from about 410 g/l to about 540 g/l, from about 420 g/l to about 540 g/l, from about 430 g/l to about 540 g/l, from about from about 440 g/l to about 540 g/l, from about 450 g/l to about 540 g/l, from about 460 g/l to about 540 g/l, from about 470 g/l to about 540 g/l, from about 480 g/l to about 540 g/l, from about 480 g/l to about 530 g/l, or from about 480 g/l to about 520 g/l on an acid equivalent basis. In these and other embodiments, the total glyphosate loading of the concentrate is about 480 g/l, about 500 g/l, about 520 g/l, or about 530 g/l on an acid equivalent basis.

In accordance with the present invention, the aqueous glyphosate concentrate compositions and/or tank mix compositions typically include at least one surfactant to enhance the herbicidal effectiveness of the glyphosate and/or any co-herbicide such as dicamba in spray formulations. As noted above, the pH of the glyphosate concentrated composition affects the degree to which one or more surfactants may be incorporated into the aqueous herbicidal concentrate composition. It has been observed that many conventional surfactants cannot be successfully incorporated into the aqueous herbicidal concentrate composition as compared to concentrate compositions having a lower pH. More specifically, it has been discovered that some surfactants conventionally used in the art in combination with glyphosate are difficult to successfully incorporate into a stable concentrate composition without precipitation or phase separation when the pH of the concentrate is above about 5. Nevertheless, certain classes of surfactants and surfactant combinations have been found to provide stable aqueous herbicidal concentrate compositions for use in conjunction with the present invention. Accordingly, in various embodiments, the glyphosate concentrate composition comprises one or more surfactants as described below.

Surfactants that may be incorporated into the concentrate include a quaternary ammonium salts of formula (I):

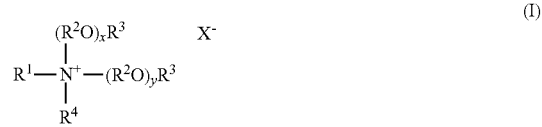

wherein $R^1$ is hydrocarbyl or substituted hydrocarbyl having from 1 to about 30 carbon atoms; $R^2$ in each of the $(R^2O)_x$ and $(R^2O)_y$ groups is independently $C_2$-$C_4$ alkylene; $R^3$ is hydrogen, or a linear or branched alkyl group having from 1 to about 4 carbon atoms; $R^4$ is hydrocarbyl or substituted hydrocarbyl having from 1 to about 30 carbon atoms; x and y are independently an average number from 1 to about 40; and $X^-$ is an agriculturally acceptable anion. In this context, preferred $R^1$ and $R^4$ hydrocarbyl groups are linear or branched alkyl, linear or branched alkenyl, linear or branched alkynyl, aryl, or aralkyl groups. Preferably, $R^1$ and $R^4$ are independently a linear or branched alkyl or linear or branched alkenyl group having from 1 to about 25 carbon atoms; $R^2$ in each of the $(R^2O)_x$ and $(R^2O)_y$ groups is independently $C_2$-$C_4$ alkylene; $R^3$ is hydrogen, methyl or ethyl; and the sum of x and y is an average number from about 2 to about 30. More preferably, $R^1$ and $R^4$ are independently a linear or branched alkyl group having from 1 to about 22 carbon atoms; $R^2$ in each of the $(R^2O)_x$ and $(R^2O)_y$ groups is independently ethylene or propylene; $R^3$ is hydrogen or methyl; and the sum of x and y is an average number from about 2 to about 20. Even more preferably, $R^1$ is a linear or branched alkyl group having from about 8 to about 22 carbon atoms; $R^4$ is a linear or branched alkyl group having from 1 to about 22 carbon atoms; $R^2$ in each of the $(R^2O)_x$ and $(R^2O)_y$ groups is independently ethylene or propylene; $R^3$ is hydrogen or methyl; and x is an average number from about 2 to about 20. Most preferably, $R^1$ is a linear or branched alkyl group having from about 8 to about 22 carbon atoms; $R^4$ is a linear or branched alkyl group having from 1 to about 6 carbon atoms; $R^2$ in each of the $(R^2O)_x$ and $(R^2O)_y$ groups is independently ethylene or propylene; $R^3$ is hydrogen or methyl; and x is an average number from about 2 to about 15; or $R^1$ and $R^4$ are independently a linear or branched alkyl group having from about 8 to about 22 carbon atoms; $R^2$ in each of the $(R^2O)_x$ and $(R^2O)_y$ groups is independently ethylene or propylene; $R^3$ is hydrogen or methyl; and x is an average number from about 5 to about 15.

One example of a preferred dialkoxylated quaternary ammonium surfactant is ETHOQUAD C-12 (a cocoalkylmethylbis(2-hydroxyethyl) ammonium chloride surfactant available from Akzo Nobel). In various embodiments, the surfactant or surfactant system may include a solvent or other additives. For example, when ETHOQUAD C-12 is incorporated into the aqueous herbicidal concentrate composition, it may be added as a mixture containing diethylene glycol (DEG) or polyethylene glycol (PEG). Therefore, in certain embodiments, the surfactant comprises ETHOQUAD C-12 dissolved in diethylene glycol or polyethylene glycol (e.g., a mixture containing 75 wt. % ETHOQUAD C-12 and 25 wt. % diethylene glycol or polyethylene glycol). Other examples of preferred quaternary ammonium surfactants that can be used to form stable aqueous glyphosate and dicamba salt concentrate compositions are ARQUAD T27W (a tallow alkyltrimethyl ammonium chloride) and ARQUAD C33W (a trimethyl coco ammonium chloride), which are available from Akzo Nobel.

In other embodiments, the surfactant comprises an alkoxylated tertiary etheramine of formula (II):

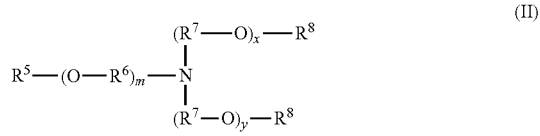

(II)

wherein $R^5$ is a hydrocarbyl or substituted hydrocarbyl having from about 4 to about 22 carbon atoms; $R^6$ and $R^7$ are each independently a hydrocarbylene having 2, 3, or 4 carbon atoms; each $R^8$ is independently hydrogen or $C_{1-6}$ alkyl, m is an average number from about 1 to about 10; and the sum of x and y is an average value ranging from about 2 to about 60. $R^5$ is preferably an alkyl having an average value ranging from about 4 to about 22 carbon atoms, more preferably from about 8 to about 22 carbon atoms, and still more preferably from about 10 to about 20 carbons atoms, for example coco, tallow, oleyl, and stearyl. Sources of the $R^5$ group include, for example, coco or tallow, or $R^5$ may be derived from synthetic hydrocarbyls, such as decyl, dodedecyl, tridecyl, tetradecyl, hexadecyl, or octadecyl groups. The number m is preferably from about 1 to 5, such as 2 to 3. $R^6$ and $R^7$ are preferably independently ethylene, propylene, isopropylene, and are preferably ethylene. $R^8$ is preferably hydrogen. The sum of x and y is preferably an average value ranging from about 2 to about 25.

One preferred example of an alkoxylated tertiary etheramine surfactant is SURFONIC AGM 550 available from Huntsman Petrochemical Corporation wherein $R^5$ is $C_{12-14}$, $R^6$ is isopropyl, $R^7$ is ethylene, $R^8$ is hydrogen, m is 2 and the sum of x and y is 5. Other examples of preferred alkoxylated tertiary etheramine surfactants that can be used to form stable aqueous glyphosate concentrate compositions are ETHOMEEN T20S (a tallow amine ethoxylate), ETHOMEEN C-15, ETHOMEEN C-12 (a coco amine ethoxylate), and AROMOX C12W (a cocobis(2-hydroxyethyl)amine oxide, based on coco amine+2 EO), all available from Akzo Nobel.

In various embodiments, the surfactant comprises an alkylpolysaccharide. Suitable alkylpolysaccharide surfactants have the structure of formula (III):

(III)

wherein $R^9$ is a straight or branched chain substituted or unsubstituted hydrocarbyl selected from alkyl, alkenyl, alkylphenyl, alkenylphenyl having from about 4 to about 22 carbon atoms. The sug moiety is a saccharide residue, and may be an open or cyclic (i.e., pyranose) structure. The saccharide may be a monosaccharide having 5 or 6 carbon atoms, a disaccharide, an oligosaccharide or a polysaccharide. Examples of suitable saccharide moieties, including their corresponding pyranose form, include ribose, xylose, arabinose, glucose, galactose, mannose, telose, gulose, allose, altrose, idose, lyxose, ribulose, sorbose (sorbitan), fructose, and mixtures thereof. Examples of suitable disaccharides include maltose, lactose and sucrose. Disaccharides, oligosaccharides and polysaccharides can be a combination of two or more identical saccharides, for example maltose (two glucoses) or two or more different saccharides, for example sucrose (a combination of glucose and fructose). The degree of polymerization, u, is an average number from 1 to about 10, from 1 to about 8, from 1 to about 5, from 1 to about 3, and from 1 to about 2. As known to those skilled in the art, as depicted in formula (III), $R^9$ is linked to an oxygen atom of the sug moiety. In various particular embodiments, the alkylpolysaccharide surfactant may be an alkylpolyglucoside (APG) surfactant of formula (III) wherein: $R^9$ is a branched or straight chain alkyl group preferably having from 4 to 22 carbon atoms, more preferably from 8 to 18 carbon atoms, or a mixture of alkyl groups having an average value within the given range; sug is a glucose residue (e.g., a glucoside); and u is from 1 to about 5, and more preferably from 1 to about 3. In various embodiments, the surfactant comprises an APG of formula (III) wherein $R^9$ is a branched or straight chain alkyl group having from 8 to 10 carbon atoms or a mixture of alkyl groups having an average value within the given range and u is from 1 to about 3.

Examples of surfactants of formula (III) are known in the art. For example, one preferred surfactant is AGNIQUE PG8107-G (AGRIMUL PG 2067) available from BASF.

Representative alkylpolysaccharide surfactants are presented in the table below wherein for each surfactant sug in formula (III) is a glucose residue.

| Trade name | $R^9$ | u |
|---|---|---|
| APG 225 | $C_{8-12}$ alkyl | 1.7 |
| APG 325 | $C_{9-11}$ alkyl | 1.5 |

-continued

| Trade name | $R^9$ | u |
| --- | --- | --- |
| APG 425 | $C_{8-16}$ alkyl | 1.6 |
| APG 625 | $C_{12-16}$ alkyl | 1.6 |
| GLUCOPON 600 | $C_{12-16}$ alkyl | 1.4 |
| PLANTAREN 600 | $C_{12-14}$ alkyl | 1.3 |
| PLANTAREN 1200 | $C_{12-16}$ alkyl | 1.4 |
| PLANTAREN 1300 | $C_{12-16}$ alkyl | 1.6 |
| PLANTAREN 2000 | $C_{8-16}$ alkyl | 1.4 |
| AGRIMUL PG 2076 | $C_{8-10}$ alkyl | 1.5 |
| AGRIMUL PG 2067 | $C_{8-10}$ alkyl | 1.7 |
| AGRIMUL PG 2072 | $C_{8-16}$ alkyl | 1.6 |
| AGRIMUL PG 2069 | $C_{9-11}$ alkyl | 1.6 |
| AGRIMUL PG 2062 | $C_{12-16}$ alkyl | 1.4 |
| AGRIMUL PG 2065 | $C_{12-16}$ alkyl | 1.6 |
| BEROL AG 6202 | 2-ethyl-1-hexyl | |

In various embodiments, one or more amidoalkylamine surfactants may be included to enhance the stability of the aqueous herbicidal concentrate compositions. The amidoalkylamine surfactants have the general structure of formula (IV):

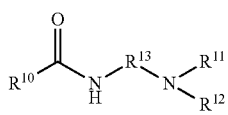

(IV)

wherein $R^{10}$ is a hydrocarbyl or substituted hydrocarbyl having from 1 to about 22 carbon atoms, $R^{11}$ and $R^{12}$ are each independently hydrocarbyl or substituted hydrocarbyl having from 1 to about 6 carbon atoms and $R^{13}$ is hydrocarbylene or substituted hydrocarbylene having from 1 to about 6 carbon atoms.

In preferred embodiments, $R^{10}$ is preferably an alkyl or substituted alkyl having an average value of carbon atoms between about 4 to about 20 carbon atoms, preferably an average value between about 4 and about 18 carbon atoms, from about 4 to about 12 carbon atoms, more preferably an average value from about 5 to about 12 carbon atoms, and still more preferably an average value from about 5 to about 10 carbon atoms. The $R^{10}$ alkyl group may be derived from a variety of sources that provide alkyl groups having from about 4 to about 18 carbon atoms, for example, the source may be butyric acid, valeric acid, caprylic acid, capric acid, coco (comprising mainly lauric acid), myristic acid (from, e.g., palm oil), soy (comprising mainly linoleic acid, oleic acid, and palmitic acid), or tallow (comprising mainly palmitic acid, oleic acid, and stearic acid). In some embodiments, the amidoalkylamine surfactant may comprise a blend of amidoalkylamines having alkyl chains of various lengths from about 5 carbon atoms to about 12 carbon atoms. For example, depending upon the source of the $R^{10}$ alkyl group, an amidoalkylamine surfactant may comprise a blend of surfactants having $R^{10}$ groups that are 5 carbon atoms in length, 6 carbon atoms in length, 7 carbon atoms in length, 8 carbon atoms in length, 9 carbon atoms in length, 10 carbon atoms in length, 11 carbon atoms in length, and 12 carbon atoms in length, longer carbon chains, and combinations thereof. In other embodiments, the amidoalkylamine surfactant may comprise a blend of surfactants having $R^{10}$ groups that are 5 carbon atoms in length, 6 carbon atoms in length, 7 carbon atoms in length, and 8 carbon atoms in length. In some alternative embodiments, the amidoalkylamine surfactant may comprise a blend of surfactants having $R^{10}$ groups that are 6 carbon atoms in length, 7 carbon atoms in length, 8 carbon atoms in length, 9 carbon atoms in length, and 10 carbon atoms in length. In other embodiments, the amidoalkylamine surfactant may comprise a blend of surfactants having $R^{10}$ groups that are 8 carbon atoms in length, 9 carbon atoms in length, 10 carbon atoms in length, 11 carbon atoms in length, and 12 carbon atoms in length.

In preferred embodiments, $R^{11}$ and $R^{12}$ are independently preferably an alkyl or substituted alkyl having from 1 to about 4 carbon atoms. $R^{11}$ and $R^{12}$ are most preferably independently an alkyl having from 1 to about 4 carbon atoms, and most preferably methyl. $R^{13}$ is preferably an alkylene or substituted alkylene having from 1 to about 4 carbon atoms. $R^{13}$ is most preferably an alkylene having from 1 to about 4 carbon atoms, and most preferably n-propylene.

In one preferred amidoalkylamine surfactant, $R^{10}$ is $C_{5-10}$, i.e., an alkyl group having 5 carbon atoms, 6 carbon atoms, 7 carbon atoms, 8 carbon atoms, 9 carbon atoms, 10 carbon atoms, or a blend of any of these, (from about 6 carbon atoms to about 10 carbon atoms); $R^{11}$ and $R^{12}$ are each methyl; and $R^{13}$ is n-propylene (i.e., $C_{6-10}$ amidopropyldimethylamine).

In order to sufficiently compatibilize and increase the amount of surfactant incorporated into the aqueous glyphosate concentrate compositions of the present invention, it may be useful to utilize a surfactant system comprising a combination of surfactants. For example, an alkoxylated tertiary etheramine surfactant or a quaternary ammonium salt surfactant may be combined with a non-ionic alkylpolysaccharide (e.g., alkylpolyglucoside or APG) surfactant to further compatibilize and increase the amount of surfactant incorporated into the glyphosate concentrate compositions. Alkylpolysaccharide surfactants are generally reported to be less effective in enhancing herbicidal activity as compared to cationic or amphoteric surfactants when used as the sole surfactant of solution concentrate formulations of a glyphosate salt. Advantageously, however, the inclusion of an alkylpolysaccharide surfactant, as described above, allows a higher concentration of an alkoxylated tertiary etheramine surfactant or quaternary ammonium salt surfactant and/or higher total surfactant concentration to be incorporated into the glyphosate concentrate compositions to take advantage of its improved efficacy in enhancing the herbicidal effectiveness of the glyphosate.

Another option to compatibilize and increase the amount of one or more alkoxylated amine surfactants, such as an alkoxylated tertiary etheramine surfactant or an alkoxylated quaternary ammonium surfactant, into the glyphosate concentrate compositions is to include one or more amidoalkylamine surfactants, which are efficient coupling agents for these surfactants. Employing a surfactant combination comprising an amidoalkylamine surfactant coupled with at least one other co-surfactant (such as an alkoxylated tertiary etheramine surfactant or an alkoxylated quaternary ammonium surfactant) not only improves herbicidal effectiveness of the glyphosate but also the long term storage stability of the concentrates.

In certain embodiments, the aqueous glyphosate concentrate composition contains a quaternary ammonium salt surfactant of formula (I) and an alkylpolyglucoside surfactant of formula (III), as described above. In other embodiments, the aqueous glyphosate concentrate composition contains a surfactant system comprising an alkoxylated tertiary etheramine surfactant of formula (II) and an amidoalkylamine surfactant of formula (IV), as described above.

Typically, the aqueous glyphosate concentrate composition contains at least about 1 wt. %, at least about 2 wt. %, at least about 3 wt. %, at least about 4 wt. %, or at least about 5 wt. % of surfactant. In various embodiments, the glyphosate concentrate composition contains from about 1 wt. % to about 20 wt. %, from about 2.5 wt. % to about 20 wt. %, from about 5 wt. % to about 20 wt. %, from about 2.5 wt. % to about 15 wt. %, from about 2.5 wt. % to about 10 wt. %, from about 5 wt. % to about 15 wt. %, or from about 5 wt. % to about 15 wt. % of surfactant.

The aqueous glyphosate concentrate compositions of the present invention are typically formulated to exhibit good storage stability at relatively low temperatures, relatively high temperatures, and/or over a wide temperatures range such that the compositions remain relatively clear without precipitation or phase separation after prolonged storage. In various embodiments, the concentrate compositions exhibit good storage stability at a temperature of less than about 0° C., less than about −10° C., less than about −20° C., or less than about −20° C. Additionally or alternatively, the concentrate compositions exhibit good storage stability at a temperature of at least about 25° C., at least about 40° C., at least about 55° C., or at least about 60° C. In various embodiments, the concentrate compositions exhibit good storage stability from about −30° C. to about 80° C., from about −30° C. to about 70° C., from about −30° C. to about 60° C., from about −10° C. to about 90° C., from about −10° C. to about 70° C., from about −10° C. to about 60° C., from about 0° C. to about 90° C., from about 0° C. to about 70° C., or from about 0° C. to about 60° C. In these embodiments, the concentrate compositions exhibit good storage stability over the period of at least about one week, at least about two weeks, at least about three weeks, or at least about four weeks.

The glyphosate concentrate compositions may further comprise other conventional adjuvants, excipients or additives known to those skilled in the art. These other additives or ingredients may be introduced into the compositions of the present invention to provide or improve certain desired properties or characteristics of the formulated product. Hence, the herbicidal concentrate composition may further comprise one or more additional ingredients selected from, without limitation, foam-moderating agents, preservatives or anti-microbials, antifreeze agents, solubility-enhancing agents, dyes, and thickening agents. For example, in various embodiments the aqueous herbicidal concentrate composition includes a foam-moderating agent such as SAG 1572 (a silicone antifoam emulsion available from Momentive). Typically the concentration of foam-moderating agent in the aqueous herbicidal concentrate composition is less than about 0.1 wt. % or less than about 0.05 wt. % (e.g., about 0.01 wt. %).

The aqueous glyphosate concentrate composition of the present invention may be prepared by a process that includes adding base to a glyphosate salt concentrate (i.e., monobasic salt concentrate). Alternatively, the glyphosate salt concentrates can be prepared by adding neutralizing base directly to glyphosate acid wet cake and then dissolving the mixture of wet cake and base in water. As discussed, the glyphosate concentrate composition contains glyphosate that is neutralized using a molar excess of base to fully neutralize the acidic site of glyphosate having the lowest pKa and at least a portion of the acidic site having the second lowest pKa. Generally less than two molar equivalents of base to glyphosate (e.g., prepared using about 1.5 molar equivalents of base to neutralize 1.5 acidic sites of glyphosate). Accordingly, in various embodiments, the glyphosate salt concentrates may be prepared using molar equivalents of neutralizing base to glyphosate from about 1:1 to about 2:1, from about 1:1 to about 1.8:1, from about 1:1 to about 1.5:1, from about 1.1:1 to about 1.5:1, from about 1:1 to about 1.4:1, from about 1.2:1 to about 2:1, from about 1.2:1 to about 1.8:1, from about 1.2:1 to about 1.5:1, from about 1.2:1 to about 1.4:1, from about 1.25:1 to about 1.5:1, from about 1.25:1 to about 1.4:1, or from about 1.25:1 to about 1.35:1. In these embodiments, the neutralizing base is typically a monoacidic base such as potassium hydroxide or monoethanolamine.

The glyphosate salt concentrate can be prepared by adding additional neutralizing base corresponding to the relevant glyphosate salt to an existing aqueous glyphosate salt solution concentrate. For example, potassium hydroxide may be used to further neutralize a concentrate containing potassium glyphosate. Alternatively, the glyphosate salt concentrate can be prepared by adding additional neutralizing base that does not correspond to the relevant glyphosate salt to an existing aqueous glyphosate salt solution concentrate to prepare a mixed glyphosate salt. For example, monoethanolamine may be used to further neutralize a concentrate containing potassium glyphosate and vice versa. Additional water may be added as necessary in order to maintain the glyphosate salt in solution.

In another aspect, the present invention is directed to aqueous tank mix compositions prepared using the aqueous glyphosate concentrate composition described above. In general, the tank mix composition comprises a glyphosate component comprising a mixture of monobasic and dibasic salts of glyphosate, a dicamba component comprising a dicamba salt, a surfactant, and dilution water.

The glyphosate component of the tank mix is conveniently provided by dilution of an aqueous glyphosate concentrate composition described above. Since the glyphosate concentrate compositions of the present invention contain glyphosate neutralized to a greater degree (e.g., neutralized using a molar excess of base to fully neutralize the acidic site of glyphosate having the lowest pKa, but less than two molar equivalents of base to glyphosate), the resulting tank mix also contains a mixture of monobasic and dibasic salts of glyphosate. Thus, in various embodiments, the molar ratio of monobasic glyphosate salt to dibasic glyphosate salt is from about 1:1 to about 10:1, from about 1:1 to about 5:1, from about 1:1 to about 4:1, from about 1:1 to about 3:1, from about 1:1 to about 2:1, or from about 1.5:1 to about 3:1.

As noted, the tribasic functionality of glyphosate is capable of buffering tank mixes containing dicamba at a pH that is approximately the pH of the glyphosate solution. Accordingly, in various embodiments, the tank mix composition prepared in accordance with the present invention has a pH from about 5 to about 6.5, from about 5.2 to about 6.5, from about 5.5 to about 6.5, from about 5 to about 6, from about 5.2 to about 6, from about 5.5 to about 6, from about 5.2 to 5.8, or from about 5.2 to about 5.6.

The dicamba component of the tank mix can be provided by a dicamba salt concentrate or dilution thereof. Various dicamba salts are known in the art and include, for example, the sodium, potassium, monoethanolamine, diethanolamine, isopropylamine, diglycolamine and dimethylamine salts. In various embodiments, the tank mix composition comprises a dicamba salt selected from the group consisting of the monoethanolamine salt, diglycolamine salt, potassium salt, and mixtures thereof. In certain embodiments, the tank mix composition contains the monoethanolamine salt of dicamba. In some embodiments, the tank mix composition contains the diglycolamine salt of dicamba.

Other salts of dicamba for use in the practice of the present invention include polyamine salts such as those described in U.S. Patent Application Publication 2012/0184434, which is incorporated herein by reference for all relevant purposes. The salts described in U.S. 2012/0184434 include an anionic pesticide, such as dicamba, and a cationic polyamine of formula (A)

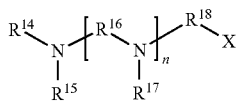

(A)

wherein $R^{14}$, $R^{15}$, $R^{17}$, $R^{19}$ and $R^{20}$ are independently H or $C_1$-$C_6$-alkyl, which is optionally substituted with OH, $R^{16}$ and $R^{18}$ are independently $C_2$-$C_4$-alkylene, X is OH or $NR^{19}R^{20}$, and n is from 1 to 20; or a cationic polyamine of formula (B)

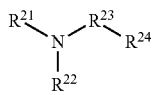

(B)

wherein $R^{21}$ and $R^{22}$ are independently H or $C_1$-$C_6$-alkyl, $R^{23}$ is $C_1$-$C_{12}$-alkylene, and $R^{24}$ is an aliphatic $C_5$-$C_8$ ring system, which comprises either nitrogen in the ring or which is substituted with at least one unit $NR^{21}R^{22}$. Examples of these cationic polyamines include tetraethylenepentamine, triethylenetetramine, diethylenetriamine, pentamethyldiethylenetriamine, N,N,N',N'',N''-pentamethyl-dipropylenetriamine, N,N-bis(3-dimethylaminopropyl)-N-isopropanolamine, N'-(3-(dimethylamino)propyl)-N,N-dimethyl-1,3-propanediamine, N,N-bis(3-aminopropyl)methylamine, N-(3-dimethylaminopropyl)-N,N-diisopropanolamine, N,N,N'-trimethylaminoethyl-ethanolamine, aminopropylmonomethylethanolamine, and aminoethylethanolamine. Accordingly, in various embodiments, the tank mix composition comprises a dicamba salt comprising a cationic polyamine of formula A or B above.

As previously discussed, off-site movement is a known problem of spray formulations containing salts of dicamba. Under certain conditions of application, dicamba can migrate from the application site to adjacent crop plants. As noted above, the volatility of dicamba can increase when tank mixed using conventional glyphosate concentrate compositions. In accordance with the present invention, it has been discovered that dicamba volatility of tank mixes of dicamba and glyphosate may be reduced when the glyphosate component of the tank mix is provided by a glyphosate concentrate composition described herein. Using the glyphosate concentrate composition in a tank mix containing glyphosate and dicamba typically provides greater than about a 40%, 50%, 60% or even 75% reduction in volatility when compared to conventional tank mixes of potassium or monoethanolamine glyphosate with diglycolamine salt of dicamba (e.g., a tank mix of CLARITY available from BASF and ROUNDUP WEATHERMAX available from Monsanto).

The tank mix composition may contain various combinations of glyphosate and dicamba salts. However, in accordance with some embodiments, certain combinations of glyphosate and dicamba salts are selected in order to achieve stable herbicidal compositions and provide other advantages as described herein. In various embodiments, the tank mix composition comprises glyphosate in the form of the monoethanolamine salt and a dicamba salt selected from the group consisting of the diglycolamine salt, monoethanolamine salt, potassium salt and mixtures thereof. In these and other embodiments, the tank mix composition comprises the monoethanolamine salt of glyphosate and the diglycolamine salt of dicamba. In still other embodiments, the tank mix composition contains glyphosate in the form of the potassium salt and a dicamba salt selected from the group consisting of the diglycolamine salt, monoethanolamine salt, potassium salt and mixtures thereof. In certain embodiments, the counter-ion of the glyphosate salt component and the dicamba salt component of the tank mix composition are the same. For example, the tank mix composition can include glyphosate and dicamba both in the form of the monoethanolamine or potassium salt of the herbicidal active ingredients.

Generally, the tank mix compositions of the present invention include glyphosate and dicamba in relatively equal proportions or an excess of glyphosate on an acid equivalent (a.e.) basis. In various embodiments, the acid equivalent weight ratio of glyphosate salt to dicamba salt ranges from about 1:1 to about 5:1, from about 1:1 to about 3:1, from about 1.5:1 to about 3:1, from about 1.5:1 to about 2.5:1, or from about 1.5:1 to about 2:1. In certain embodiments, the acid equivalent weight ratio of glyphosate salt to dicamba salt is about 1.5:1, about 2:1, or about 3:1.

The tank mixture composition of the present invention comprises dilution water. The amount of dilution water may be adjusted depending upon various factors such as the type of unwanted plants to be controlled and application rate. Typically, dilution water is present in the tank mix such that the total herbicide content (glyphosate and dicamba) is from about 0.1 to about 200, from about 0.1 to about 100, or from about 50 to about 100 g a.e./l herbicide active. In various embodiments, the tank mix composition has a total herbicide concentration (glyphosate and dicamba) no greater than about 20% or about 10% by weight acid equivalent In accordance with the methods of using the tank mix composition of the present invention, the tank mix composition may be applied to the foliage of unwanted plants as a spray formulation solution by methods known in the art. The tank mix is applied to the foliage of a plant or plants at an application rate sufficient to give a commercially acceptable rate of weed control. Depending on plant species and growing conditions, the period of time required to achieve a commercially acceptable rate of weed control can be as short as a week or as long as three weeks, four weeks or 30 days. The application rate is usually expressed as amount of herbicide per unit area treated, e.g., grams acid equivalent per hectare (g a.e./ha) and can readily be determined by those skilled in the art.

The tank mixture comprising dicamba and dilution of the aqueous glyphosate concentrate composition of the present invention can be applied pre-planting of the crop plant, such as from about 2 to about 3 weeks before planting glyphosate and dicamba-susceptible crop plants or crop plants not having a dicamba-resistant trait. Crop plants that are not susceptible to glyphosate and dicamba herbicides, such as corn, or plants having glyphosate-tolerant and dicamba-tolerant traits typically have no pre-planting restriction and the application mixture can be applied immediately before planting such crops. The tank mix can be applied at planting or post-emergence to crop plants having glyphosate-tolerant and dicamba-tolerant traits to control glyphosate and/or dicamba-susceptible weeds in a field of the crop plants.

EXAMPLES

The following non-limiting examples are provided to further illustrate the present invention.

Example 1

In this example, various glyphosate concentrate compositions containing mixtures of monobasic and dibasic glyphosate salts were prepared by adding additional base (e.g., monoethanolamine (MEA) or potassium hydroxide) to stock glyphosate salt concentrates. Various surfactants listed in Table 1 were added to the concentrates to assess compatibility. The concentrates prepared are listed in Table 2. In addition to the ingredients listed in Table 2, the concentrates also contained iron citrate dopant (from about 6.5 to 7 grams/liter).

The stability of the solutions was observed upon mixing and any precipitation or phase separation was noted. The dilute pH (5 wt. % a.e. glyphosate), neat pH (concentrate pH without dilution) and cloud point of selected stable solutions were measured. The pH measurements were obtained by immersing the probe of calibrated pH meter into each concentrate formulation and/or dilution thereof and recording the digital reading. The pH measurements were made using a Mettler Toledo model SevenEasy pH meter with a Thermo Scientific ROSS Sure-flow pH probe. The pH meter was calibrated in accordance with the manufacturer's recommended protocol at pH 4 and pH 7 using standard buffer solutions. Table 2 presents these measurements.

TABLE 1

| Surfactant | Surfactant Type |
|---|---|
| C-6350 | 55/45 blend of ETHOMEEN T20S and APA |
| ETHOMEEN T20S | tallow amine ethoxylate |
| APA | amidopropylamine |
| EAE | etheramine ethoxylate |
| AGM 590 | 90/10 blend of etheramine ethoxylate and ETHOMEEN $C_{12}$ |
| ETHOMEEN C12 | cocoamine ethoxylate |
| ETHOQUAD C12 | cocoalkylmethylbis(2-hydroxyethyl)ammonium chloride |
| AGNIQUE PG 8107 | $C_{8-10}$ alkyl polyglycoside |

TABLE 2

| Glyphosate Concentrate No. | Glyphosate salt | Glyphosate loading (g a.e./l) | Added Base | Added Base Conc. (g/l) | Surfactant(s) | Surfactant(s) Conc. (g/l) | Dilute pH (5 wt. % a.e. sol.) | Neat pH | Cloud Point ° C. | Clear and Stable at room temperature? |
|---|---|---|---|---|---|---|---|---|---|---|
| 1 | K | 540 | MEA | 27 | C-6350 | 109.3 | 4.97 | NA | >80 | Yes |
| 2 | K | 540 | MEA | 54 | C-6350 | 109.3 | 4.97 | NA | >80 | Yes |
| 3 | K | 540 | MEA | 30.6 | C-6350 | 110.1 | 5.02 | NA | NA | NA |
| 4 | K | 540 | MEA | 54.5 | C-6350 | 110.3 | 5.26 | NA | NA | NA |
| 5 | K | 540 | MEA | 68.1 | C-6350 | 110.3 | 5.37 | NA | NA | NA |
| 6 | K | 540 | MEA | 81.8 | C-6350 | 110.4 | 5.51 | NA | 48 | Yes |
| 7 | K | 540 | MEA | 95.5 | C-6350 | 110.5 | 5.69 | NA | NA | Yes |
| 8 | K | 540 | MEA | 82.0 | C-6350 | 110.7 | 5.58 | NA | 47 | Yes |
| 9 | K | 540 | MEA | 82.0 | AGM 590 | 110.7 | NA | NA | NA | No, cloudy |
| 10 | K | 540 | MEA | 82.0 | EAE ETHOMEEN C12 | 88.6 22.2 | NA | NA | NA | No, cloudy |
| 11 | K | 480 | MEA | 70 | EAE | 98 | NA | NA | NA | No, cloudy |
| 12 | K | 540 | MEA | 30.6 | C-6350 | 110.0 | 5.06 | 5.57 | >80 | Yes |
| 13 | K | 540 | MEA | 54.5 | C-6350 | 110.3 | 5.3 | 5.99 | >80 | Yes |
| 14 | K | 540 | MEA | 68.2 | C-6350 | 110.4 | 5.41 | 6.26 | 73 | Yes |
| 15 | K | 540 | MEA | 68.2 | ETHOMEEN T20S APA | 55.3 55.3 | 5.57 | 6.28 | 67 | Yes |
| 16 | K | 480 | MEA | 70.5 | C-6350 | 98.4 | 5.49 | 6.67 | >80 | Yes |
| 17 | K | 480 | MEA | 70.5 | C-6350 | 98.4 | NA | NA | NA | No |
| 18 | K | 540 | MEA | 81.9 | ETHOQUAD C12 | 110.6 | 5.33 | NA | NA | NA |
| 19 | K | 540 | MEA | 95.8 | ETHOQUAD C12 | 110.8 | 5.48 | 6.34 | >80 | Yes |
| 20 | K | 540 | KOH | 105.4 | ETHOMEEN T20S APA | 55 55 | NA | NA | NA | No |
| 21 | K | 540 | KOH | 123.1 | ETHOQUAD C12 | 109.9 | 5.27 | NA | NA | Yes |
| 22 | K | 540 | KOH | 111.5 | ETHOMEEN T20S APA | 55.1 55.1 | NA | NA | NA | No |
| 23 | K | 540 | KOH | 132.4 | ETHOQUAD C12 | 110.1 | 5.29 | NA | NA | Yes |
| 24 | K | 540 | KOH | 135.1 | ETHOQUAD C12 | 110.6 | 5.28 | NA | NA | NA |
| 25 | K | 540 | KOH | 135.1 | ETHOQUAD C12 | 91 | NA | NA | NA | NA |
| 26 | K | 540 | KOH | 135.1 | ETHOQUAD C12 | 75.6 | 5.33 | NA | NA | NA |
| 27 | K | 540 | KOH | 74 | ETHOQUAD C12 | 110 | 5.34 | 5.89 | >80 | Yes |
| 28 | K | 540 | KOH | 74 | ETHOQUAD C12 | 75 | 5.35 | 6.2 | >80 | Yes |
| 29 | K | 540 | MEA | 95.8 | ETHOQUAD C12 | 75.3 | 5.46 | 6.26 | >80 | Yes |
| 30 | K | 540 | MEA | 81.9 | ETHOMEEN T20S APA | 37.5 37.5 | 5.46 | 6.23 | >80 | Yes |
| 31 | K | 540 | KOH | 147.1 | ETHOQUAD C12 | 110.7 | NA | NA | NA | NA |
| 32 | K | 480 | KOH | 139.51 | ETHOQUAD C12 AGNIQUE PG 8107 | 24.59 73.77 | NA | NA | NA | NA |
| 33 | K | 480 | KOH | 139.51 | ETHOQUAD C12 | 66.97 | NA | NA | NA | NA |

TABLE 2-continued

| Glyphosate Concentrate No. | Glyphosate salt | Glyphosate loading (g a.e./l) | Added Base | Added Base Conc. (g/l) | Surfactant(s) | Surfactant(s) Conc. (g/l) | Dilute pH (5 wt. % a.e. sol.) | Neat pH | Cloud Point ° C. | Clear and Stable at room temperature? |
|---|---|---|---|---|---|---|---|---|---|---|
| 34 | K | 480 | KOH | 139.51 | ETHOQUAD C12 AGNIQUE PG 8107 | 16.74 50.23 | 6.03 | NA | NA | Yes |
| 35 | K | 480 | KOH | 139.51 | ETHOQUAD C12 | 98.36 | 5.99 | NA | NA | Yes |

NA: Not measured or not observed.

Example 2

This example describes experiments conducted to measure the effect on dicamba concentration in the gas phase (air) volatilized from spray applications of tank mixes prepared from selected glyphosate concentrates prepared in accordance with Example 1 and diglycolamine (DGA) dicamba solutions. The tank mixes were prepared by diluting DGA dicamba concentrate (CLARITY 39.7% a.e., available from BASF) with water. Glyphosate concentrate was then mixed with the diluted DGA dicamba solution. Sufficient dilution water was added to prepare tank mixes containing 1.2 wt. % a.e. dicamba and 2.4 wt. % a.e. glyphosate. Conventional tank mixes containing (a) 1.2 wt. % a.e. DGA dicamba (CLARITY) and (b) 1.2 wt. % a.e. DGA dicamba (CLARITY) plus 2.4 wt. % a.e. potassium glyphosate (WEATHERMAX available from Monsanto) were prepared to serve as controls for the experiments. The tank mixes were tested for dicamba volatility using the humidome method as follows.

Humidomes (24.25 L) were obtained from Hummert International (Part Nos 14-3850-2 for humidomes and 11-3050-1 for 1020 flat tray) and modified by cutting a 2.2 cm diameter hole on one end approximately 5 cm from the top to allow for insertion of a glass air sampling tube (22 mm OD) containing a polyurethane foam (PUF) filter cut to 30 mm in length. The sampling tube was secured with a VITON o-ring on each side of the humidome wall. The air sampling tube external to the humidome was fitted with tubing that was connected to a vacuum manifold immediately prior to sampling.

The flat tray beneath the humidome was filled 1 liter of sifted dry or wet 50/50 soil (50% Redi-Earth and 50% US 10 Field Soil) to a depth of about 1 cm. The flat tray bottom containing the dicamba formulation on soil was covered with a humidome lid and the lid was secured with clamps. The assembled humidomes were placed in a temperature and humidity controlled environment and connected to a vacuum manifold through the air sampling line. Air was drawn through the humidome and PUF at a rate of 2 liters per minutes (LPM) for 24 hours at which point the air sampling was stopped. The humidomes were then removed from the controlled environment and the PUF filter was removed. The PUF filter was extracted with 20 mL of methanol and the solution was analyzed for dicamba using LC-MS methods known in the art.

To measure the dicamba concentration in the gas phase (air) volatilized from the spray applications of the tank mixes, the tank mixes were sprayed at an application rate of 1.0 lb/acre a.e. at 10 gallons per acre. The growth chambers were set at 35° C. and 40% RH. For each tank mix four separate humidome boxes were sprayed to have 4 replicates measurements for each formulation. Table 3 provides the mean concentration of dicamba in air for each tank mix.

TABLE 3

| Tank Mix No. | Glyphosate Concentrate from Example 1 | Glyphosate Concentration (wt. % a.e.) | Dicamba Concentration (wt. % a.e.) | Dicamba Concentration in Air (ng/l) | Standard Deviation |
|---|---|---|---|---|---|
| 1A | 12 | 2.4 | 1.2 | 0.513 | 0.269 |
| 1B | 15 | 2.4 | 1.2 | 0.056 | 0.003 |
| CLARITY + WEATHERMAX (Control 1C) | — | 2.4 | 1.2 | 1.309 | 0.089 |
| CLARITY (Control 1D) | — | 2.4 | 1.2 | 0.069 | 0.038 |
| 2A | 34 | 2.4 | 1.2 | 0.051 | 0.005 |
| CLARITY + WEATHERMAX (Control 2B) | — | 2.4 | 1.2 | 2.401 | 0.536 |
| CLARITY (Control 2C) | — | 2.4 | 1.2 | 0.081 | 0.011 |
| 3A | 35 | 2.4 | 1.2 | 0.069 | 0.018 |
| CLARITY + WEATHERMAX (Control 3B) | — | 2.4 | 1.2 | 1.631 | 0.224 |
| CLARITY (Control 3C) | — | 2.4 | 1.2 | 0.171 | 0.067 |

The results show that the spray solutions prepared from glyphosate concentrates 12, 15, 34, and 35 exhibited significantly lower dicamba volatility when compared to prior art spray solutions of CLARITY plus WEATHERMAX.

Unless otherwise indicated, the term "hydrocarbyl" describes organic moieties consisting exclusively of the elements carbon and hydrogen and preferably containing 1 to about 50 carbon atoms, preferably 1 to about 30 carbon atoms, and even more preferably 1 to about 20 carbon atoms, including branched or unbranched, saturated or unsaturated and cyclic species. These moieties include alkyl, alkenyl, alkynyl, and aryl moieties optionally substituted with other aliphatic or cyclic hydrocarbon groups, such as alkaryl, alkenaryl and alkynaryl.

Unless otherwise indicated, the term "substituted hydrocarbyl" describes hydrocarbyl moieties that are substituted with at least one atom other than carbon, including moieties in which a carbon chain or ring atom is substituted with a hetero atom such as nitrogen, oxygen, silicon, phosphorous, boron, sulfur, or a halogen atom. Unless otherwise stated, these substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A method of preparing an aqueous tank mix composition comprising a glyphosate component and a dicamba component, the method comprising:
   combining an aqueous glyphosate concentrate composition, a dicamba composition comprising one or more salts of dicamba and dilution water to form the tank mix composition, wherein the glyphosate concentrate composition comprises (a) a mixture of monobasic and dibasic salts of glyphosate, wherein the molar ratio of monobasic glyphosate salt to dibasic glyphosate salt is from about 1:1 to about 3:1 and the monobasic and dibasic salts of glyphosate are selected from the group consisting of monoethanolamine salts, potassium salts, and mixtures thereof, at a glyphosate loading from about 360 grams acid equivalent per liter to about 550 grams acid equivalent per liter (g. a.e./l.) and (b) one or more surfactants, and wherein the pH of a 5 wt. % acid equivalent dilution of the glyphosate concentrate composition is from about 5 to about 6.5 and wherein the tank mix composition has a total herbicide concentration of no greater than about 10% by weight a.e.

2. The method of claim 1 wherein the pH of a 5 wt. % acid equivalent dilution of the glyphosate concentrate composition is from about 5.2 to about 5.8.

3. The method of claim 1 wherein the monobasic and dibasic salts of glyphosate are the potassium salts of glyphosate.

4. The method of claim 1 wherein the monobasic and dibasic salts of glyphosate are the monoethanolamine salts of glyphosate.

5. The method of claim 1 wherein the ratio of the total weight of the glyphosate salts on an acid equivalence basis to the total weight of the dicamba salt on an acid equivalence basis in the tank mix composition is from about 1:1 to about 5:1.

6. The method of claim 1 wherein the dicamba salt is selected from the group consisting of a monoethanolamine salt, diglycolamine salt, potassium salt, and mixtures thereof.

7. The method of claim 1 wherein the glyphosate loading of the glyphosate concentrate composition is from about 400 g a.e./l to about 540 g a.e./l.

8. The method of claim 1 wherein the glyphosate loading of the glyphosate concentrate composition is from about 450 g a.e./l to about 540 g a.e./l.

9. The method of claim 1 wherein a molar ratio from about 1.25:1 to about 1.35:1 of a glyphosate neutralizing base to glyphosate is used to prepare the monobasic and dibasic salts of glyphosate of the glyphosate concentrate composition.

10. The method of claim 1 wherein the molar ratio of monobasic glyphosate salt to dibasic glyphosate salt is from about 1.5:1 to about 3:1.

11. The method of claim 1 wherein the molar ratio of monobasic glyphosate salt to dibasic glyphosate salt is from about 1:1 to about 2:1.

12. The method of claim 10 wherein the monobasic and dibasic salts of glyphosate are the potassium salts of glyphosate.

13. The method of claim 6 wherein the dicamba salt is the diglycolamine salt.

14. The method of claim 1 wherein the surfactant comprises a quaternary ammonium salt of formula (I):

wherein $R^1$ is hydrocarbyl or substituted hydrocarbyl having from 1 to about 30 carbon atoms; $R^2$ in each of the $(R^2O)_x$ and $(R^2O)_y$ groups is independently $C_2$-$C_4$ alkylene; $R^3$ is hydrogen, or a linear or branched alkyl group having from 1 to about 4 carbon atoms; $R^4$ is hydrocarbyl or substituted hydrocarbyl having from 1 to about 30 carbon atoms; x and y are independently an average number from 1 to about 40; and $X^-$ is an agriculturally acceptable anion.

15. The method of claim 14 wherein the $R^1$ and $R^4$ hydrocarbyl groups are independently linear or branched alkyl, linear or branched alkenyl, linear or branched alkynyl, aryl, or aralkyl groups.

16. The method of claim 14 wherein $R^2$ in each of the $(R^2O)_x$ and $(R^2O)_y$ groups is independently $C_2$-$C_4$ alkylene, or ethylene or propylene; $R^3$ is hydrogen, methyl or ethyl;

and the sum of x and y is an average number from about 2 to about 30 or from about 2 to about 20.

17. The method of claim 14 wherein $R^1$ is a linear or branched alkyl group having from about 8 to about 22 carbon atoms; $R^4$ is a linear or branched alkyl group having from 1 to about 22 carbon atoms; $R^2$ in each of the $(R^2O)_x$ and $(R^2O)_y$ groups is independently ethylene or propylene; $R^3$ is hydrogen or methyl; and x is an average number from about 2 to about 20.

18. The method of claim 14 wherein the surfactant comprises a cocoalkylmethylbis(2-hydroxyethyl)ammonium chloride salt.

19. The method of claim 1 wherein the surfactant comprises an alkoxylated tertiary etheramine of formula (II):

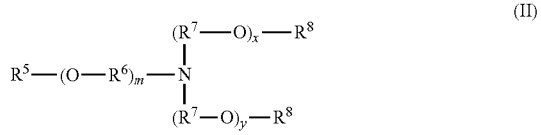

(II)

wherein $R^5$ is a hydrocarbyl or substituted hydrocarbyl having from about 4 to about 22 carbon atoms; $R^6$ and $R^7$ are each independently a hydrocarbylene having 2, 3, or 4 carbon atoms; each $R^8$ is independently hydrogen or $C_{1-6}$ alkyl, m is an average number from about 1 to about 10; and the sum of x and y is an average value ranging from about 2 to about 60.

20. The method of claim 19 wherein $R^5$ is an alkyl having from about 4 to about 22 carbon atoms, $R^6$ and $R^7$ are independently ethylene, propylene, isopropylene; $R^8$ is hydrogen; m is an average value ranging from about 1 to 5; and the sum of x and y is an average value ranging from about 2 to about 25.

21. The method of claim 19 wherein $R^5$ is $C_{12-14}$; $R^6$ is isopropyl; $R^7$ is ethylene; $R^8$ is hydrogen; m is 2; and the sum of x and y is 5.

22. The method of claim 1 wherein the surfactant comprises an alkylpolysaccharide.

23. The method of claim 22 wherein the alkylpolysaccharide surfactant has the structure of formula (III):

(III)

wherein $R^9$ is a straight or branched chain substituted or unsubstituted hydrocarbyl having from about 4 to about 22 carbon atoms selected from the group consisting of alkyl, alkenyl, alkylphenyl, and alkenylphenyl; the sug moiety is a saccharide residue; and u is an average number from 1 to about 10.

24. The method of claim 23 wherein the alkylpolysaccharide surfactant is an alkylpolyglucoside wherein $R^9$ is a branched or straight chain alkyl group having from 4 to 22 carbon atoms, or a mixture thereof; sug is a glucose residue; and u is from 1 to about 5 or from 1 to about 3.

25. The method of claim 1 wherein the surfactant comprises an amidoalkylamine of formula (IV):

(IV)

wherein $R^{10}$ is a hydrocarbyl or substituted hydrocarbyl having from 1 to about 22 carbon atoms, $R^{11}$ and $R^{12}$ are each independently hydrocarbyl or substituted hydrocarbyl having from 1 to about 6 carbon atoms, and $R^{13}$ is hydrocarbylene or substituted hydrocarbylene having from 1 to about 6 carbon atoms.

26. The method of claim 1 wherein the glyphosate concentrate composition has surfactant concentration from about 1 wt. % to about 20 wt. %.

27. The method of claim 1 wherein the glyphosate concentrate composition comprises:

(1) a quaternary ammonium salt of formula (I):

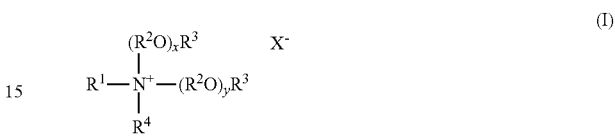

(I)

wherein $R^1$ is hydrocarbyl or substituted hydrocarbyl having from 1 to about 30 carbon atoms; $R^2$ in each of the $(R^2O)_x$ and $(R^2O)_y$ groups is independently $C_2$-$C_4$ alkylene; $R^3$ is hydrogen, or a linear or branched alkyl group having from 1 to about 4 carbon atoms; $R^4$ is hydrocarbyl or substituted hydrocarbyl having from 1 to about 30 carbon atoms; x and y are independently an average number from 1 to about 40; and $X^-$ is an agriculturally acceptable anion; and (2) an alkylpolysaccharide surfactant has the structure of formula (III):

(III)

wherein $R^9$ is a straight or branched chain substituted or unsubstituted hydrocarbyl having from about 4 to about 22 carbon atoms selected from the group consisting of alkyl, alkenyl, alkylphenyl, and alkenylphenyl; the sug moiety is a saccharide residue; and u is an average number from 1 to about 10.

28. The method of claim 1 wherein the glyphosate concentrate composition comprises:

(1) an alkoxylated tertiary etheramine of formula (II):

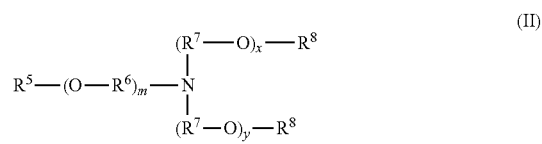

(II)

wherein $R^5$ is a hydrocarbyl or substituted hydrocarbyl having from about 4 to about 22 carbon atoms; $R^6$ and $R^7$ are each independently a hydrocarbylene having 2, 3, or 4 carbon atoms; each $R^8$ is independently hydrogen or $C_{1-6}$ alkyl, m is an average number from about 1 to about 10; and the sum of x and y is an average value ranging from about 2 to about 60; and (2) an amidoalkylamine of formula (IV):

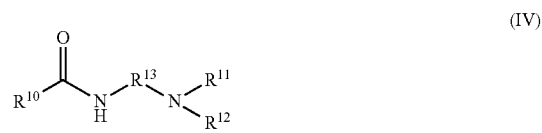

(IV)

wherein $R^{10}$ is a hydrocarbyl or substituted hydrocarbyl having from 1 to about 22 carbon atoms, $R^{11}$ and $R^{12}$ are each independently hydrocarbyl or substituted hydrocarbyl having from 1 to about 6 carbon atoms, and $R^{13}$ is hydrocarbylene or substituted hydrocarbylene having from 1 to about 6 carbon atoms.

29. A tank mix composition comprising:

a mixture of monobasic and dibasic salts of glyphosate, wherein the molar ratio of monobasic glyphosate salt to dibasic glyphosate salt is from about 1:1 to about 3:1 and the monobasic and dibasic salts of glyphosate are selected from the group consisting of monoethanolamine salts, potassium salts, and mixtures thereof;

one or more salts of dicamba;

dilution water; and a surfactant, wherein the tank mix composition has a total herbicide concentration of no greater than about 10% by weight a.e. and a pH from about 5.2 to about 5.8.

30. The tank mix composition of claim 29 wherein the surfactant is selected from the group consisting of:

(1) a quaternary ammonium salt of formula (I):

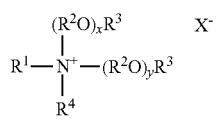

wherein $R^1$ is hydrocarbyl or substituted hydrocarbyl having from 1 to about 30 carbon atoms; $R^2$ in each of the $(R^2O)_x$ and $(R^2O)_y$ groups is independently $C_2$-$C_4$ alkylene; $R^3$ is hydrogen, or a linear or branched alkyl group having from 1 to about 4 carbon atoms; $R^4$ is hydrocarbyl or substituted hydrocarbyl having from 1 to about 30 carbon atoms; x and y are independently an average number from 1 to about 40; and $X^-$ is an agriculturally acceptable anion;

(2) an alkoxylated tertiary etheramine of formula (II):

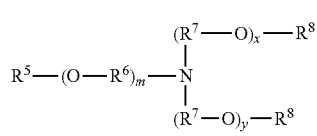

wherein $R^5$ is a hydrocarbyl or substituted hydrocarbyl having from about 4 to about 22 carbon atoms; $R^6$ and $R^7$ are each independently a hydrocarbylene having 2, 3, or 4 carbon atoms; each $R^8$ is independently hydrogen or $C_{1-6}$ alkyl, m is an average number from about 1 to about 10; and the sum of x and y is an average value ranging from about 2 to about 60;

(3) an alkylpolysaccharide of formula (III):

wherein $R^9$ is a straight or branched chain substituted or unsubstituted hydrocarbyl having from about 4 to about 22 carbon atoms selected from the group consisting of alkyl, alkenyl, alkylphenyl, and alkenylphenyl; the sug moiety is a saccharide residue; and u is an average number from 1 to about 10;

(4) an amidoalkylamine of formula (IV):

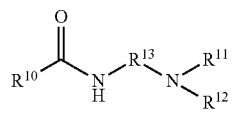

wherein $R^{10}$ is a hydrocarbyl or substituted hydrocarbyl having from 1 to about 22 carbon atoms, $R^{11}$ and $R^{12}$ are each independently hydrocarbyl or substituted hydrocarbyl having from 1 to about 6 carbon atoms, and $R^{13}$ is hydrocarbylene or substituted hydrocarbylene having from 1 to about 6 carbon atoms; and combinations thereof.

* * * * *